US008784779B2

(12) United States Patent
Schaeffer-Korbylo et al.

(10) Patent No.: US 8,784,779 B2
(45) Date of Patent: Jul. 22, 2014

(54) COLOR CHANGE OF CHALCONE-CONTAINING ORAL CARE FORMULATIONS

(75) Inventors: Lyndsay Schaeffer-Korbylo, Flemington, NJ (US); Gregory Szewczyk, Flemington, NJ (US); Laurence Du-Thumm, Princeton, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 13/520,751

(22) PCT Filed: Jan. 6, 2011

(86) PCT No.: PCT/US2011/020370
§ 371 (c)(1),
(2), (4) Date: Oct. 16, 2012

(87) PCT Pub. No.: WO2011/085098
PCT Pub. Date: Jul. 14, 2011

(65) Prior Publication Data
US 2013/0195772 A1 Aug. 1, 2013

Related U.S. Application Data

(60) Provisional application No. 61/293,079, filed on Jan. 7, 2010.

(51) Int. Cl.
*A61K 8/35* (2006.01)
*A61Q 11/00* (2006.01)
(52) U.S. Cl.
USPC ............. 424/10.3; 424/49; 424/401; 568/325
(58) Field of Classification Search
USPC .......................................... 536/8; 424/49, 58
See application file for complete search history.

(56) References Cited

U.S. PATENT DOCUMENTS

| | | | |
|---|---|---|---|
| 3,739,064 A * | 6/1973 | Rizzi | |
| 5,116,602 A | 5/1992 | Robinson et al. | |
| 5,683,678 A | 11/1997 | Heckert et al. | |
| 2003/0138511 A1 | 7/2003 | Yamamoto et al. | |
| 2006/0078633 A1 | 4/2006 | Na et al. | |
| 2006/0099237 A1 | 5/2006 | Modak et al. | |
| 2006/0222601 A1 | 10/2006 | Sabnis et al. | |
| 2008/0227867 A1 * | 9/2008 | Ley et al. | 514/685 |

FOREIGN PATENT DOCUMENTS

| | | |
|---|---|---|
| AU | A-24595/88 | 6/1989 |
| EP | 1764363 | 3/2007 |
| JP | 55-129215 | 10/1980 |
| JP | 58-213706 A | 12/1983 |
| JP | 1999-501918 | 2/1999 |
| JP | 2002-121122 | 4/2002 |
| JP | 2003-122645 | 4/2003 |
| JP | 2005-298357 A | 10/2005 |
| JP | 2007-320926 | 12/2007 |
| JP | 2008-031076 | 2/2008 |
| WO | WO 99/66796 | 12/1999 |
| WO | WO 2005/009352 | 2/2005 |
| WO | WO 2005/123023 | 12/2005 |
| WO | WO 2006/071404 | 7/2006 |
| WO | WO 2006/105260 | 10/2006 |
| WO | WO2009/093584 | 7/2009 |
| WO | WO 2011/019342 | 2/2011 |
| WO | WO 2011/075136 | 6/2011 |

OTHER PUBLICATIONS

Aas et al., 2005, "Defining the Normal Bacterial Flora of the Oral Cavity", Journal of Clinical Microbiology,. 43(11) 1:5721-5732.
Bambeke et al., 2003, "Antibiotic, Efflux Pumps in Prokaryotic Cells: Occurrence, Impact on Resistance and Strategies for the Future of Antimicrobial Therapy", Joinnal of Antimicrobial Chemotherapy, 51:1055-1065.
Batovska et al, 2009, "Examination of Growth Inhibitory Properties of Synthetic Chalcones for which Antibacterial Activity was Predicted", European Journal of Medicinal Chemistry, 44(5):2211-2218.
Brehm-Stecher et al., 2003, "Sensitization of *Staphylococcus Aureus* and *Escherichia Coli* to Antibiotics by the Sesquiterpenoids Nerolidol Famesol, Bisabolol and Apritone", Antimicrobial Agents & Chemotherapy, 47(10):3357-3360.
Database GNPD Mintel, 2006, "Oral Spray", XP002616749, Accession No. 590881.
Database GNPD Mintel, 2007, "Toothpaste", XP002616750, Accession No. 702824.
Database GNPD Mintel, 2008, "Toothpaste for Sensitive Teeth", XP002016748, Accession No. 999752.
Hunter-Rinderle et al., 1997, "Evaluation of Cetylpyridinium Chloride Containing Mouthwashes, Using in vitro Disk Retention and ex vivo plague Glycolysis Methods", Journal of Clinical Dentistry, 8:107-113.
Isaaac et al., 1980, "Chamomile Therapy—Experience and Confirmation"Dtsch, Apoth. Ztg 120:567-570.

(Continued)

*Primary Examiner* — Walter Webb
(74) *Attorney, Agent, or Firm* — Rena Patel

(57) ABSTRACT

Oral care compositions and methods are described in which the composition includes a chalcone color change component, which may be phenyl-3-methoxy-4-hydroxystyryl ketone. The color change component is induced to change colors by addition of saliva and/or by a change in pH of the composition. The composition and methods provide benefits including providing visual cues to the user.

7 Claims, 1 Drawing Sheet

(56) References Cited

OTHER PUBLICATIONS

Isaac et al., 1980, "Old and New Methods of Chamomile Therapy", Die Medizinche Welt, 31(31-32):1145-1149, in German Kaatz et al., 1997, "Mechanisms of Fluroquinolone Resistance in Genetically Related Strains of *Staphylococcus Aureus*", Antimicrobial Agents & Chemotherapy, 41(12),2733-2737.

Keusch, 2003, "Anthocyannis as pH Indicators & Complexiing Agents", http://www.demochem.de/p26_anth-e.html.

Lee et al., 2000, "Interplay Between Efflux Pumps May Provide Either Additive or Multiplicative Effects on Drug Resistance", Journal of Bacteriology, 182(11):3142-3150.

Li et al., 2000, "Interplay Between the MexA-MexB-OprM Multidrug Efflux System and the Outer Membrane Barrier in the Multiple Antibiotic Resistance of Pseudomonas Aeruginosa", Journal of Antimicrobial Chemotherapy, 45:433-436.

Lomovskaya et al., 1999, "Use of a Genetic Approach to Evaluate the Consequences of Inhibition of Efflux Pumps in Pseudomonas Aeruginosa", Antimicrobial Agents & Chemotherapy, 4310:1340-1346.

Luppold, 1984, "*Matricaria Chamomilla*—an Old and New Medicinal Plant", Pharmazie in Unserer Zeit 13(3):65-70.

Moncada et al., 2004, "Tuning the Photochromic Properties of a Flavylium Compound by pH", European Journal of Organic Chemistry, 2004(2):304-312.

Nikaido, 1994, "Prevention of Drug Access to Bacterial Targets: Permeability Barriers and Active Efflux", Science 267:382-388.

PCT/US09/053500—ISR and Written Opinion mailed Feb. 3, 2011.

PCT/US2009/068688—ISR and Written Opinion mailed Oct. 5, 2010.

PCT/US2009/068688—Written Opinion mailed Dec. 5, 2011.

PCT/US2011/02370—ISR and Written Opinion mailed May 7, 2012.

Sato et al., 1992, "Antimicrobial Activity of DU-6859, a New Potent Fluroquinolene, Against Clinical Isolates", Antimicrobial Agents & Chemotherapy, 36(7):1491-1498.

Shintre et al., 2006, "Efficacy of an Alcohol-Based Healthcare Hand Rub Containing Synergistic Combination of Famesol and Benzethonium Chloride", International Journal of Hygiene Environmental Health, 209(5):477-487.

Spratt, 1994, "Resistance to Antibodies Mediated by Target Alterations", Science 264(5157):388-393.

Szalontai et al., 1975, "Further Details on the Bactericidal and Fungicidal Action of Biologically Active Substances of *Matriciaria chamomillia* I. ", Dtsch. Apoth. Ztg 115:912.

Szalontai et al., 1975, "Further Details on the Bactericidal and Fungicidal Action of Biologically Active Substances of *Matriciaria chamomillia* I. ", Pharmaz. Ztg. 120:982.

Tanaka et al., 1993, "Antimicrobial Activity of DV-7751a, a New Flueroquimolene", Antimicrobial Agents & Chemotherapy, 37(10):2112-2118.

Urban et al., 1987, Definition of Antibiotics, Roche Lexiken Medizin, 80-81, in German.

Webber et al., 2003, "The Importance of Efflux Pumps in Bacterial Antibiotic Resistance", Journal of Antimicrobial Chemotherapy. 51:(1)9-11.

Yun et al., 2002, "In Vitro and In Vivo Antibacterial Activities of DW286, a New Fluoronaphthyridone Antibiotic", Antimicrobial Agents & Chemotherapy, 46(9):3071-3074.

Shin-Keshohingaku (New Cosmetics) Jan. 18, 2001, p. 180-184.

Die Pharmazie, Jul. 1991, 46(7):542-543.

Singh et al., "Antiinflammatory Actions of Methyl-and Phenyl-3-methoxy-4-hydroxy Styryl Ketones," Arzneimittel Forschung/Drug Research, Apr. 1987, 37(1):435-440.

* cited by examiner

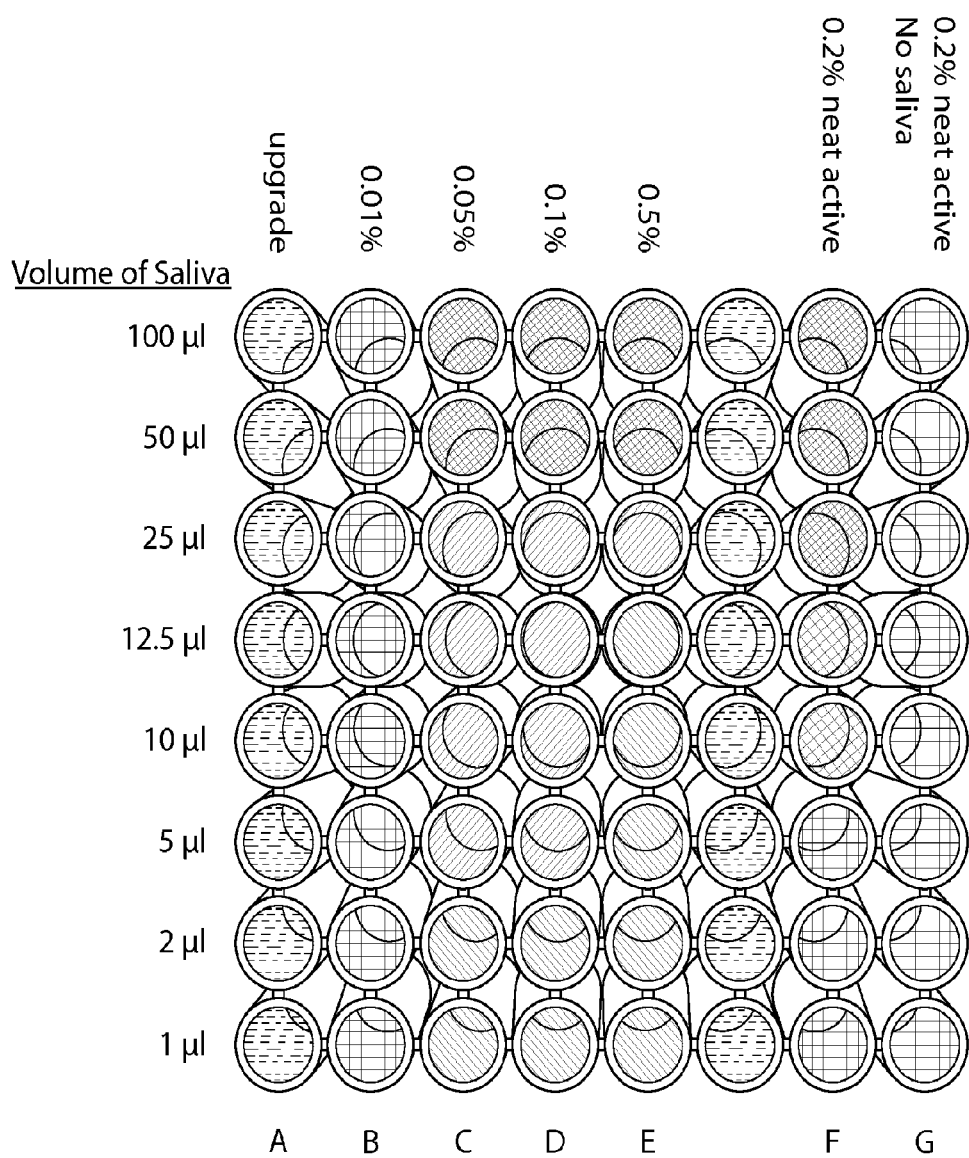

COLOR CHANGE OF CHALCONE-CONTAINING ORAL CARE FORMULATIONS

CROSS REFERENCE TO RELATED APPLICATIONS

This application claims priority to U.S. Provisional Patent Application No. 61/293,079, filed on Jan. 7, 2010, which is incorporated herein by reference.

BACKGROUND

This application relates to oral care compositions, and more particularly to compositions comprising chalcone compounds. Specifically, the invention relates to oral care compositions containing phenyl-3-methoxy-4-hydroxystryryl ketone as a pH induced color change component. Such compositions include for example, dentifrices.

The use of mouthwash is adjunctive to toothbrushing. However, the use of mouthwash does not require as much active interaction as does brushing one's teeth. It also does not provide a signal that anything has happened during the use aside from mouth feel that is usually astringent or burning.

SUMMARY

The present invention provides, in various embodiments, oral care compositions comprising a chalcone color change component, in which the composition changes color by contact with saliva and/or by a change in pH. More specifically, the chalcone color change component is phenyl-3-methoxy-4-hydroxystyryl ketone (CHAK4). In one embodiment, the oral care composition is a mouthwash.

Yet another feature of the invention relates to a method of making an oral care composition comprising phenyl-3-methoxy-4-hydroxystyryl ketone (CHAK4) as a color change component.

Still another feature of the invention relates to a method of providing oral health benefits to an oral surface.

BRIEF DESCRIPTION OF THE FIGURE

FIG. 1 is a gray-scale depiction of a plate showing the effects of saliva on the color of CHAK4 containing mouthwashes.

DETAILED DESCRIPTION

The present invention provides compositions and methods for administration to, or use with, a human or other animal subject. Preferably, specific materials and compositions to be used in this invention are, accordingly, pharmaceutically- or cosmetically-acceptable. As used herein, such a "pharmaceutically acceptable" or "cosmetically acceptable" component is one that is suitable for use with humans and/or animals to provide the desired therapeutic, sensory, decorative, or cosmetic benefit without undue adverse side effects (such as toxicity, astringent taste, irritation, and allergic response) commensurate with a reasonable benefit/risk ratio. The following definitions and non-limiting guidelines should be considered in reading and interpreting the description of this invention set forth herein.

All references cited herein are hereby incorporated by reference in their entirety.

The description and specific examples, while indicating embodiments of the invention, are intended for purposes of illustration only and are not intended to limit the scope of the invention. Recitation of multiple embodiments having stated features is not intended to exclude other embodiments having additional features, or other embodiments incorporating different combinations of the stated features. Specific Examples are provided for illustrative purposes of how to make, use and practice the compositions and methods of this invention and, unless explicitly stated to recite activities that have been done (i.e., using the past tense), are not intended to be a representation that given embodiments of this invention have, or have not, been performed.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention. As used herein, the word "include," and its variants, is intended to be non-limiting, such that recitation of items in a list is not to the exclusion of other like items that may also be useful in the materials, compositions, devices, and methods of this invention. In a similar manner, the description of certain advantages or disadvantages of known materials and methods is not intended to limit the scope of the embodiments to their exclusion. Indeed, certain embodiments may include one or more known materials or methods, without suffering from the disadvantages discussed herein.

As used herein, the term "comprising" means that other steps and other components that do not affect the end result may be utilized. The term "comprising" encompasses the expressions "consisting of," and "consisting essentially of." The expression "effective amount," as used herein denotes an amount of a compound or composition sufficient to significantly induce a positive benefit, preferably an oral health benefit, but low enough to avoid serious side effects, i.e., to provide a reasonable benefit to risk ratio, within the sound judgment of a person having ordinary skill in the art. The use of singular identifiers such as "the," "a," or "an" is not intended to be limiting solely to the use of a single component, but may include multiple components.

As referred to herein, an "oral care composition" is any composition that is suitable for administration or application to a human or animal subject for enhancing the health, hygiene or appearance of the subject, including the prevention or treatment of any physiologic condition or disorder, and providing sensory, decorative or cosmetic benefits and combinations thereof. By "oral care composition" as used herein is meant a composition for which the intended use can include oral care, oral hygiene, or oral appearance, or for which the intended method of use can comprise administration to the oral cavity.

The oral care compositions of the various embodiments preferably are in the form of a dentifrice. The term "dentifrice" as used throughout this description, denotes a paste, gel, or liquid formulation.

The expressions "carrier" or "aqueous carrier" as used throughout this description denote any safe and effective materials for use herein. Such materials include, for example, thickening agents, humectants, ionic active ingredients, buffering agents, anticalculus agents, abrasive polishing materials, peroxide sources, alkali metal bicarbonate salts, surfactants, titanium dioxide, coloring agents, flavor systems, sweetening agents, antimicrobial agents, herbal agents, desensitizing agents, stain reducing agents, and mixtures thereof.

All percentages and ratios used herein are by weight of the oral care composition, unless otherwise specified. All measurements are made at 25° C., unless otherwise specified.

Chalcones are a family of naturally occurring compounds found in a number of plant species. All chalcone compounds share a common aromatic ketone core. Chalcones have been shown to have antibacterial, antifungal, antitumor and anti-inflammatory properties.

Chalcone derivatives for use in oral compositions are described in co-pending International Application Serial No. PCT/US2009/068688, entitled "Chalcones as Enhancer of Antimicrobial Agents,", hereby incorporated by reference in its entirety. The chalcone derivatives described in this co-pending patent application are believed to have the properties of enhancing efficacy in in vitro screening, when combined with various anti-infective agents using bacteria, viruses and yeast. These compositions and compounds also were efficacious when tested in vivo using mice and guinea pig models infected with microorganisms.

One chalcone derivative described in this co-pending patent application is 3-(4'-Hydroxy-3'-methoxy-phenyl)-1-phenyl-prop-2-ene-1-one, also known as phenyl-3-methoxy-4-hydroxystyryl ketone, and which will be referred to herein as CHAK4. The formula for CHAK4 is as follows:

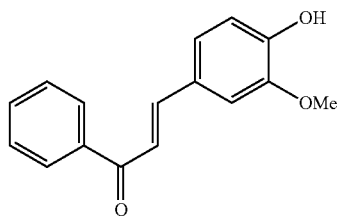 [SMILES: COc1cc(/C=C/C(=O)c2ccccc2)ccc1O]

In studies with compositions including CHAK4, the present inventors unexpectedly observed that the addition of the compositions to any surface containing human saliva produced an immediate and distinctive color change. This surprising discovery that saliva causes a color shift to a composition comprising CHAK4 led the present inventors to believe that pH had an effect on the color of a composition comprising CHAK4.

A solution with a pH of 3.8 comprising CHAK4 and no additional colorant has a yellow color. As the pH of the solution increases towards neutral, the color shifts from the yellow at a pH of 3.8 to a goldenrod color at a pH of 4.8 to a red color at a pH of 6.8. The present inventors' research demonstrated that unique to CHAK4 is its ability to change color in response to small fluctuations in pH. This effect on pH on the color of a composition comprising CHAK4 may be used in oral care compositions as a feedback signal.

In one embodiment, the present invention provides an oral care composition comprising CHAK4. The oral care composition may comprise from 0.01% to 10% CHAK4, or from 0.05 to 5%, or from 0.1% to 1%, or from 0.1% to 0.5%. In one embodiment, the oral care composition comprises from 0.01% to 0.05% CHAK4.

The pH of the oral care composition may be from 2.0 to 12.0. In various embodiments, the pH of the oral care composition may be from 3.5 to 5.0. The normal pH of saliva is near neutral. Addition of saliva to an acidic solution comprising CHAK4 would increase the pH level towards basic, thereby causing a color shift in the solution. The color change may serve as a feedback signal to a user that the composition is working.

In another embodiment, colorant may be added to the oral composition comprising CHAK4. The additional colorants may be added to compositions having CHAK4 to provide a variety of starting color aesthetics. The same color shifting effect of CHAK4 is also observed in solutions comprising additional colorants.

In certain embodiments, the compositions of the present invention are oral care compositions, suitable for administration to the oral cavity. Such compositions include dentifrices, mouthwashes, dental gels, lozenges, beads, gums, oral strips, mints, liquid toothpastes, sprays, paint-on gels, lip balms, whitening strips, breath strips, oral chews, and combinations thereof. An oral care composition disclosed herein can be used, for example, for cavity prevention, whitening, plaque prevention or reduction, gingivitis prevention or reduction, tartar control, sensitivity prevention or reduction, or breath malodor prevention or reduction, and stain prevention.

In a preferred embodiment, the oral composition is in the form of a mouthwash. In a mouthwash preparation, the vehicle may comprise alcohol or may be alcohol free. In one embodiment, the vehicle is a water-alcohol mixture. Generally, the weight ratio of water to alcohol is in the range of from 1:1 to 20:1, preferably 3:1 to 10:1 and more preferably 4:1 to 6:1. The total amount of water-alcohol mixture in this type of preparation is typically in the range of from 70 to 99.9% by weight. The alcohol preferably is a non-toxic alcohol such as ethanol or isopropanol. Humectants such as glycerine and sorbitol may be present in amounts of 10-30% by weight. Liquid dentifrices typically contain 50-85% of water, may contain 0.5-20% by weight of non-toxic alcohol and may also contain 10-40% by weight of humectant such as glycerine and/or sorbitol. Reference to sorbitol refers to the material typically available commercially in 70% aqueous solutions. Ethanol is the preferred non-toxic alcohol.

Organic surface-active agents also may be used in the compositions of the present invention to achieve increased prophylactic action, assist in achieving thorough and complete solvent dispersion of antiplaque antibacterial agent throughout the oral cavity, and render the instant compositions more cosmetically acceptable. The organic surface-active material is preferably anionic, nonionic or ampholytic in nature, and it is preferred to employ as the surface-active agent a detersive material that imparts to the composition detersive and foaming properties. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2-dihydroxy propane sulfonate, higher fatty acid esters of taurine and the substantially saturated higher aliphatic acyl amides of lower aliphatic amino carboxylic acid compounds, such as those having 12 to 16 carbons in the fatty acid, alkyl or acyl radicals, and the like. Examples of suitable taurines and amides are N-methyl-N-cococyl taurate, N-methyl-N-oleoyl taurate, N-methyl-N-palmitoyl-taurate, N-lauroyl sarcosinate, and the sodium, potassium, and ethanolamine salts of N-lauroyl, N-myristoyl, or N-palmitoyl sarcosine which should be substantially free from soap or similar higher fatty acid material. The taurine compounds particularly assist solution. The use of the sarcosinate compounds in the oral compositions of the present invention is particularly advantageous since these materials exhibit a prolonged and marked effect in the inhibition of acid formation in the oral cavity due to carbohydrate breakdown in addition to exerting some reduction in the solubility of tooth enamel in acid solutions.

Examples of water-soluble nonionic surfactants are condensation products of ethylene oxide with various reactive hydrogen-containing compounds reactive therewith having long hydrophobic chains (e.g. aliphatic chains of 12 to 20 carbon atoms), which condensation products ("ethoxamers") contain hydrophilic polyoxyethylene moieties, such as condensation products of poly(ethylene oxide) with fatty acids, fatty alcohols, fatty amides, polyhydric alcohols (e.g. sorbitan monostearate) and polypropyleneoxide (e.g. Pluronic materials). Amphoteric or zwitterionic surfactants also may be used in the various embodiments.

The mouthwash composition also may contain an anticaries effective amount of fluoride ion source sufficient to supply 25 ppm to 5,000 ppm of fluoride ions. The sources of fluoride ions, or fluorine-providing components are well known in the art as anticaries agents. These compounds may be slightly soluble in water or more preferably fully water-soluble. They are characterized by an ability to release fluoride ions in water and by substantial freedom from undesired reaction with other compounds of the oral preparation.

The amount of fluorine-providing compound is dependent to some extent upon the type of compound, its solubility, and the type of oral preparation, but it must be a non-toxic amount, generally 0.0005% to 3.0% in the preparation. In a mouthwash preparation, an amount of such compound which releases up to 5,000 ppm of F ion by weight of the preparation is considered satisfactory. Any suitable effective anticaries minimum amount of such compound may be used, but it is preferable to employ sufficient compound to release 100 to 2,000 ppm, more preferably 300 to 1,500 ppm of fluoride ion.

Any suitable flavoring or sweetening material may also be employed. Examples of suitable flavoring constituents are flavoring oils, e.g. oil of spearmint, peppermint, wintergreen, sassafras, clove, sage, eucalyptus, marjoram, cinnamon, lemon, and orange, and methyl salicylate. Suitable sweetening agents include sucrose, lactose, maltose, xylitol, sodium cyclamate, perillatrine, AMP (aspartyl phenyl alanins, methyl ester), saccharine and the like. Suitably, flavor and sweetening agents may each or together comprise from 0.001% to 5% or more of the preparation, each being typically 0.1-2.5%.

Various other materials may be incorporated in the oral preparations of this invention such as whitening agents, preservatives, silicones, chlorophyll compounds and/or ammoniated material such as urea, diammonium phosphate, and mixtures thereof. These adjuvants, where present, are incorporated in the preparations in amounts which do not substantially adversely affect the properties and characteristics desired. Significant amounts of zinc, magnesium and other metal salts and materials, generally soluble, which would complex with active components of the instant invention are to be avoided.

It will be understood that, as is conventional, the oral preparations are to be sold or otherwise distributed in suitably labelled packages. Thus a container of mouthwash will have a label describing it, in substance, as a mouthrinse or mouthwash and having directions for its use; and a liquid toothpaste will usually be in a collapsible or drip tube, typically aluminum, lined lead or plastic, or other dispenser for metering out the contents, having a label describing it, in substance, as a liquid toothpaste or dentifrice.

In various embodiments, the present invention provides methods for administering a functional material to a human or animal subject in need thereof, comprising topically applying to said subject a composition comprising CHAK4. As referred to herein, "administering" refers to any method by which a composition is applied on or administered to the subject. In various embodiments, the administration is topical, wherein the composition is applied to an external surface of the subject, such as to a surface of the oral cavity (e.g., teeth, gingival, and tongue). The specific route and method of administration will depend, of course, on the intended use of the composition.

In various embodiments, the present invention provides methods for the treatment of an oral care condition. As referred to herein, an "oral care condition" is any disorder or condition which can be prevented or treated by administration of a composition to the oral cavity, including disorders or conditions of the teeth, oral mucosa, gingiva and tongue. Such conditions include caries, gingivitis, periodontitis, and cosmetic conditions such as yellowing and malodour.

The embodiments described herein can be further understood by reference to the following non-limiting examples.

EXAMPLES

Example 1

CHAK4 was added to a starting base mouthwash formulation containing cetylpyridinum chloride that was colorless. CHAK4 added to the colorless mouthwash changed the mouthwash formulation to a yellow color. Varying concentrations of CHAK-4 were used, from 0.01%, 0.05%, 0.1% and 0.5% by weight. The color of the mouthwash formulation for the 0.05 wt % CHAK-4 produced the strongest color change, to an almost orange-like color. The remaining formulations were bright yellow.

Example 2

This example illustrates the effect of saliva on the color of a mouthwash solution comprising CHAK4. Mouthwash solutions were made in accordance with the present invention with increasing concentrations of CHAK4. 100 µl of mouthwash was added to wells on a 96 well plate. Increasing volumes of sterilized human saliva were then added to each well containing mouthwash.

As shown in FIG. 1, a systematic mixing of mouthwashes containing increasing concentrations of CHAK4 with sterilized human saliva in varying concentrations demonstrated the sensitivity of the color change in the mouthwash to relatively small amounts of saliva. A distinctive color change is observed with the addition of saliva to the mouthwash. For each of the CHAK-4 formulations, (0.01%, 0.05%, 0.1%, and 0.5% by weight), the color change became more and more pronounced with more saliva. In other words, starting at a relatively slight yellow color at 1 µl saliva, as saliva concentration increased, the color changed from yellow to more orange, with the exception of the 0.01%, in which the color became more distinctly yellow.

In the last two columns of the plate in FIG. 1 (F & G), neat active dissolved in 95% ethanol was combined with either saliva or sterile water. Mixed with sterile water, CHAK4 retains its distinctive yellow color (G). However, when mixed with saliva, there is a clear change to an orange color (F), and again for each sample, the color became more intense as the volume of saliva was increased.

Example 3

This example illustrates the effect of pH on the color of a mouthwash solution comprising 0.1% CHAK4. CHAK4 was mixed into clear mouthwash solutions and the pH adjusted. The solution was yellow at a pH of 3.8, goldenrod at a pH of 4.5, and red at a pH of 6.8. Within a relatively narrow range of pHs, it was possible to induce a color change in full mouthwash formulations containing 0.1% CHAK4.

Example 4

A typical mouthwash formulation as well as a formulation containing CHAK4 is provided in table 1. Each mouthwash formulation contained a blue dye, such that a mouthwash without CHAK4 was blue and the mouthwash formulations containing CHAK4 was green. The final formula color may be tailored depending upon the type of colorant combined with the CHAK4.

TABLE 1

| Ingredient | Standard Formula | Formula A | Formula B |
|---|---|---|---|
| Water | Balance | Balance | Balance |
| Pluronic F127 | 0.25% | 0.25% | 0.25% |
| Sorbitol | 5.5% | 0.0% | 0.0% |
| Propylene Blycol | 5.0% | 6.0% | 6.0% |
| Glycerin | 7.5% | 19.0% | 19.0% |
| Ethyl Alcohol | 6.0% | 6.0% | 6.0% |
| Sweetener | 0.001% | 0.001% | 0.001% |
| Cetylpyridinium Chloride | 0.055% | 0.055% | 0.055% |
| CHAK4 | 0.0% | 0.01% | 0.05% |
| Sodium chloride | 0.0% | 0.0% | 0.03% |
| Flavor | 0.1% | 0.1% | 0.1% |

Example 5

An in vitro study indicated that the color change in mouthwash compositions including CHAK4 can be readily induced by mixing with small amounts of saliva comparable to the amount that would be present when rinsing in actual use.

Simulated mouthrinsing was conducted by combining a 15 mL mouthwash dose with 1 mL of human saliva. Each mouthwash had a different starting color, and each displayed a perceivable color change after combining with saliva. This simulated rinsing study demonstrated that the addition of CHAK4 can yield a color change when combined with saliva in an actual usage situation. This example demonstrates the ease in which the starting aesthetic can be adjusted, while still providing a very discernable and perceivable end color.

The examples and other embodiments described herein are exemplary and not intended to be limiting in describing the full scope of compositions and methods of this invention. Equivalent changes, modifications and variations of specific embodiments, materials, compositions and methods may be made within the scope of the present invention, with substantially similar results.

The invention claimed is:

1. A method of providing oral health benefits to an oral surface of a subject comprising contacting the oral surface of the subject with an oral care composition including phenyl-3-methoxy-4-hydroxystyryl ketone (CHAK4) as a color component and an orally acceptable carrier, wherein the oral care composition is allowed to contact saliva from the oral surface to effect a change in color of the oral care composition providing a feedback signal to the subject of the oral health benefits provided to the oral surface and a signal for when to cease contacting the oral surface with the oral care composition.

2. The method of claim 1, wherein the oral care composition further comprises an antibacterial agent; and the oral health benefit is providing antibacterial activity.

3. The method of claim 2, wherein the antibacterial agent is cetylpyridinium chloride and the amount of phenyl-3-methoxy-4-hydroxystyryl ketone (CHAK4) is from 0.01 wt. % to 10 wt. %.

4. The method of claim 3, wherein the amount of phenyl-3-methoxy-4-hydroxystyryl ketone (CHAK4) is from 0.5 wt. % to 5 wt. % and the pH of the oral care composition is from 3.5 to 5.0.

5. The method of claim 4, wherein the amount of phenyl-3-methoxy-4-hydroxystyryl ketone (CHAK4) is from 0.1 wt % to 1 wt. % and the color of the oral care composition changes from yellow to red after contacting saliva from the oral surface.

6. The method of claim 4, wherein the oral care composition is a mouthwash.

7. The method of claim 4, wherein the oral care composition is a dentifrice.

* * * * *